United States Patent [19]

Schwinn et al.

[11] 4,411,794

[45] Oct. 25, 1983

[54] PROCESS FOR THE PURIFICATION OF THE BLOOD CLOTTING FACTORS, II, VII, IX AND/OR X

[75] Inventors: Horst Schwinn; Norbert Heimburger, both of Marburg; Gerhardt Kumpe, Wetter; Heinz H. Drescher, Neustadt, all of Fed. Rep. of Germany

[73] Assignee: Behringwerke Aktiengesellschaft, Marburg, Fed. Rep. of Germany

[21] Appl. No.: 340,896

[22] Filed: Jan. 19, 1982

[30] Foreign Application Priority Data

Jan. 21, 1981 [DE] Fed. Rep. of Germany ....... 3101752

[51] Int. Cl.³ ............................................ B01D 15/00
[52] U.S. Cl. .................................... 210/670; 210/691; 210/927; 260/112 B
[58] Field of Search ............... 210/670, 690, 691, 927; 260/112 B

[56] References Cited

U.S. PATENT DOCUMENTS 4,081,431 3/1978 Stephan et al. ................. 260/112 B

OTHER PUBLICATIONS

Hoag et al., "Treatment of Hemophilia B with a New Clotting-Factor Concentrate", New England Journal of Medicine, 280, pp. 581–586, Mar. 13, 1969.

*Primary Examiner*—Ivars C. Cintins
*Attorney, Agent, or Firm*—Curtis, Morris & Safford

[57] ABSTRACT

A process for purifying liquids containing blood clotting factors by adsorption of the factors on mineral adsorbents such as calcium phosphate, aluminum hydroxide gel, barium sulfate or hydroxylapatite in the presence of calcium ions followed by elution is described.

6 Claims, No Drawings

PROCESS FOR THE PURIFICATION OF THE BLOOD CLOTTING FACTORS, II, VII, IX AND/OR X

The present invention relates to a process for the purification of liquids containing blood clotting factors by adsorption on mineral adsorbents which have been described for this purpose such, as calcium phosphate, aluminum hydroxide gel, barium sulfate or hydroxylapatite in the presence of calcium ions.

It is known to enrich and to purify blood clotting factors by adsorption on anion exchangers and calcium phosphate, followed by elution, for example from plasma [cf. Soulier, J. P. et al.: Thromb. Diath. Haemorrh. Suppl. 35, 61 (1969); Burning, P. F. et al.: Hemophilia and New Hemmorrhagic States, Univ. North Carolina Press, Chapel Hill, p. 3 (1979); Bidwell, E. et al.: Br. J. Haematol. 22, 469 (1972)].

However, for the therapy of disturbances of blood coagulation, preparations of blood clotting factors of higher purity are required.

There was therefore a need to find a process by which preparations of blood clotting factors having the purity which is required nowadays could be obtained from solutions optionally heated to kill hepatitis viruses.

This task is fulfilled by adsorbing the blood clotting factors from solutions containing them on mineral adsorbents such as calcium phosphate, aluminum hydroxide gel, barium sulfate or hydroxylapatite in the presence of calcium ions, followed by elution.

The subject of the present invention therefore is a process for the purification of a blood clotting factor, which process comprises adsorbing the blood clotting factor from a solution containing it, in the presence of calcium ions, on mineral adsorbents known per se, such as aluminum hydroxide gel, barium sulfate, hydroxylapatite or, preferably, calcium phosphate, followed by elution.

To a protein solution containing the blood clotting factor in a concentration of at least 0.05 to 0.1 units/mg of protein, there is added a calcium salt in a concentration 0.05 to 2.0 mols/l, preferably 0.4 to 0.6 mol/l of calcium chloride ($CaCl_2$), and a surface-active adsorbent such as calcium phosphate, aluminum hydroxide gel, hydroxylapatite or barium sulfate in a concentration from 0.2 to 20 w/v %, preferably calcium phosphate in a concentration from 0.4 to 1 w/v %, and the batch is stirred at a pH from 6.0 to 9.0. The adsorbent is separated from the liquid, optionally washed and eluted, for example as has been described by Soulier J. P. et al. in Thromb. Diath. Haemorrh. Suppl. 35, 61 (1969).

To reach a higher yield the protein solution has to be fractionated optionally prior to the adsorption using precipitants known to the expert, it being necessary that the precipitants chosen do not alter the concentration of the calcium ions.

The process which is preferably used is superior to the previously cited processes of the art in that it uses calcium ions during the adsorption. The high affinity of the blood clotting factors to said adsorbents in the presence of calcium ions is demonstrated by the following table by using, by way of example, 0.5 mol/l of $CaCl_2$, calcium phosphate and the blood clotting factor II (prothrombin):

| Calcium phosphate concentration w/v % | F II remaining in the supernatant in % of the starting activity | |
|---|---|---|
| | without $CaCl_2$ | with $CaCl_2$ |
| 0 | 100 | 100 |
| 0.25 | 100 | 50 |
| 0.5 | 100 | 23 |
| 1.0 | 46 | 0 |
| 2.0 | 14 | — |
| 3.0 | 8 | — |

The concentration of calcium phosphate required for a quantitative adsorption is reduced more than threefold by the presence of $CaCl_2$. Unspecific adsorptions are thus practically excluded so that the blood clotting factors may be subsequently eluted in a very pure form.

Due to their knowledge of methods for the determination of the substances concerned, those skilled in the art are familiar with monitoring the measures for the enrichment and purification of the blood clotting factors adsorbed on calcium phosphate, aluminum hydroxide gel, barium sulfate or hydroxylapatite.

The activity determination of Factor II can be carried out, for example, by the method of Koller, F. et al., Dtsch. med. Wschr. 81, 516 (1956). For this purpose, one part, for example 0.1 ml of plasma deficient in Factor II, and one part of diluted normal plasma are mixed. This mixture is kept for 30 seconds at $+37°$ C. Subsequently, two parts of calcium-containing thromboplastin prepared, for example, according to German Pat. No. 2,356,493 are added and the time is determined which elapses until a clot appears. For quantitative data, the clotting time resulting with the solution containing Factor II is read off by reference to a calibration curve obtained with a dilution series of normal plasma.

One unit of Factor II corresponds to the Factor II activity of 1 ml of normal plasma.

Factor VII can be determined, for example, by the method of Koller, F. et al., Acta haemat. 6, 1 (1951). For this purpose, one part, for example 0.1 ml, of plasma deficient in Factor VII, and one part of diluted normal plasma are mixed. This mixture is kept for 30 seconds at $+37°$ C. Subsequently, two parts of calcium-containing thromboplastin prepared, for example, according to German Pat. No. 2,356,493 are added and the time is determined which elapses until a clot appears. For quantitative data, the clotting time resulting with the solution containing Factor VII is read off by reference to a calibration curve obtained with a dilution series of normal plasma.

One unit of Factor VII corresponds to the Factor VII activity of 1 ml of normal plasma.

Factor IX can be determined, for example, by the following method:

One part, for example 0.1 ml, of partial thromboplastin prepared according to German Auslegeschrift No. 2,316,430 is diluted with one part of a plasma deficient in Factor IX and with one part of diluted normal plasma. This mixture is kept for 6 minutes at 37° C. After addition of one part of a 0.025 molar calcium chloride solution that has been heated previously to 37° C., the time is determined which elapses until a clot appears. For quantitative data the clotting time resulting with the solution containing Factor IX is read off by reference to a calibration curve obtained with a dilution series of normal plasma.

One international unit (=1 IU) of Factor IX corresponds to the Factor IX activity of 1 ml of normal plasma.

Factor X can be determined, for example, by the method of Duckert, F. et al., Blood Coagulation, Hemorrhage and Thrombosis, Ed. Tocantins, L. M. and Kazal, L. A. (1964). To this end, one part, for example 0.1 ml, of a plasma deficient in Factor X and one part of dilute normal plasma are mixed. This mixture is kept for 30 seconds at +37° C. Next, two parts of calcium-containing thromboplastin prepared, for example, according to German Pat. No. 2,356,493 are added and the time is determined which ellapses until a clot appears. For quantitative data, the clotting time resulting with the solution containing Factor X is read off by reference to a calibration curve obtained with a dilution series of normal plasma.

One unit of Factor X corresponds to the Factor X activity of 1 ml of normal plasma.

Using these monitoring methods, the process conditions can be directed to the preparation of a concentrate containing the blood clotting factors which is satisfactory from the point of view of yield and purity.

When operating under the conditions preferably used, a far purer product is obtained than in the previously cited processes, while the yield is comparable, as can be seen in the following table:

|  | preparation of the blood clotting factors | | | | | | | |
|---|---|---|---|---|---|---|---|---|
|  | II | | VII | | IX | | X | |
| process | (1) | (2) | (1) | (2) | (1) | (2) | (1) | (2) |
| purity (spec. activity) unities*/mg | 0.6 | 2.0 | 0.3 | 1.0 | 0.5 | 2.5 | 0.5 | 2.5 |

*1 Unit corresponds to the activity of the coagulation factor in 1 ml of human normal citrate plasma.
(1) according to Soulier, J. P. et al.
(2) according to Example 1 of this application.

The present invention will be illustrated in greater detail in the following examples:

EXAMPLE 1

Preparation of a concentrate containing the Factors II, VII, IX and X from human plasma.

7.5 liters of a solution containing the Factors II, VII, IX and X of 500 liters of human plasma are prepared according to Soulier et al. in the presence of 1 mol/l of NaCl at pH 8. The specific activity of the Factors II, IX and X in each case has to be $\geq 0.1$ units/mg, that of Factor VII $\geq 0.05$ units.

The solution is brought to an ammonium sulfate concentration of 40 w/v %. The precipitate is centrifuged off and discarded. The supernatant is freed of sulfate ions by dialysis. Thereto there are added 0.25 kg of $CaCl_2.2H_2O$ and 0.25 kg of $Ca_3(PO_4)_2$ and the product is stirred for 30 minutes at pH 7.6. Instead of 0.25 kg of $Ca_3(PO_4)_2$, 1.3 liter of a 1 w/v % suspension of Al$(OH)_3$ may be used to obtain a comparable result. After centrifuging, the supernatant liquid is discarded and the adsorbent is washed with two 10 liter portions of 0.5 mol/l NaCl solution. The adsorbent is eluted with 1.8 liters of buffer at pH 8.0, which contains 0.2 mol/l of trisodium citrate, 0.15 mol/l of NaCl, 2 g/100 ml of glycine, 0.3 U/ml of antithrombin III and 14 IU/ml of heparin. After the addition of 0.2 g/100 ml of colloidal silica as a centrifuging aid, the eluate is separated from the adsorbent by centrifuging at 30,000 g. The residue is discarded and the supernatant liquid is dialyzed for 3 hours against 100 liters of a buffer at pH 7, containing 0.06 mol/l of NaCl, 0.02 mol/l of trisodium citrate and 2 g/100 ml of glycine. The dialyzate is tested for the activity of Factors II, VII, IX and X, is adjusted to the desired concentration, sterilized by filtration, divided into unit doses and lyophilized.

About 650 dosage units, each comprising 160 units of Factor II, of 80 units of Factor VII, 200 units of Factor IX and 140 units of Factor X are obtained from 500 liters of normal plasma.

What is claimed is:

1. A method for purifying a blood clotting factor selected from the group consisting of Factors II, VII, IX, and X, which method comprises adsorbing said blood clotting factor on a mineral adsorbent from a solution containing at least one such blood clotting factor together with calcium ions contributed by a calcium salt dissolved in said solution, and then eluting adsorbed blood clotting factor from said mineral adsorbent with a buffer of high ionic strength.

2. A method as in claim 1 wherein said dissolved calcium salt is calcium chloride.

3. A method as in claim 1 wherein said mineral adsorbent is calcium phosphate, aluminum hydroxide gel, barium sulfate, or hydroxylapatite.

4. A method as in claim 1 wherein said calcium salt is dissolved in said solution to provide calcium ions at a concentration from 0.05 to 2 moles/liter and said mineral adsorbent is added to said solution in an amount from 0.2 to 20 w/v percent at a pH from 6 to 9.

5. A method as in claim 4 wherein said dissolved calcium salt is calcium chloride.

6. A method as in claim 4 wherein said adsorbent is washed after separation from said solution and prior to elution.

* * * * *